US012584824B2

(12) United States Patent
Bosio et al.

(10) Patent No.: US 12,584,824 B2
(45) Date of Patent: Mar. 24, 2026

(54) METHOD FOR EXTRACTION OF TARGET CELLS FROM 3D TISSUE BY OPTICAL IDENTIFICATION

(71) Applicant: MILTENYI BIOTEC B.V. & CO. KG, Bergisch Gladbach (DE)

(72) Inventors: Andreas Bosio, Bergisch Gladbach (DE); Heinrich Spiecker, Bielefeld (DE)

( * ) Notice: Subject to any disclaimer, the term of this patent is extended or adjusted under 35 U.S.C. 154(b) by 841 days.

(21) Appl. No.: 17/801,148

(22) PCT Filed: Feb. 25, 2021

(86) PCT No.: PCT/EP2021/054663
§ 371 (c)(1),
(2) Date: Aug. 19, 2022

(87) PCT Pub. No.: WO2021/170710
PCT Pub. Date: Sep. 2, 2021

(65) Prior Publication Data
US 2023/0069991 A1 Mar. 9, 2023

(30) Foreign Application Priority Data

Feb. 28, 2020 (DE) ..................... 10 2020 105 311.8

(51) Int. Cl.
| | |
|---|---|
| *G01N 1/08* | (2006.01) |
| *C12Q 1/6886* | (2018.01) |
| *G01N 1/30* | (2006.01) |
| *G01N 15/14* | (2024.01) |
| *G01N 15/1433* | (2024.01) |
| *C12Q 1/6841* | (2018.01) |

(52) U.S. Cl.
CPC ............ *G01N 1/08* (2013.01); *C12Q 1/6886* (2013.01); *G01N 1/30* (2013.01); *G01N 15/1433* (2024.01); *C12Q 1/6841* (2013.01); *C12Q 2600/156* (2013.01); *G01N 2015/1497* (2013.01)

(58) Field of Classification Search
None
See application file for complete search history.

(56) References Cited

U.S. PATENT DOCUMENTS

| | | | |
|---|---|---|---|
| 2016/0314583 A1* | 10/2016 | Couch .................... | H04N 23/56 |
| 2017/0219465 A1* | 8/2017 | Deisseroth ....... | G01N 27/44743 |
| 2019/0005304 A1* | 1/2019 | Adalsteinsson .. | G01N 35/00871 |
| 2021/0104295 A1* | 4/2021 | Mitra ...................... | G01N 1/36 |

FOREIGN PATENT DOCUMENTS

| | | |
|---|---|---|
| JP | 2017/129735 | 7/2017 |
| WO | WO 2017/100374 | 6/2017 |

* cited by examiner

*Primary Examiner* — P. Kathryn Wright
(74) *Attorney, Agent, or Firm* — Jaquelin K. Spong

(57) ABSTRACT

The invention is directed to a process for extracting target cells from a three dimensional biological specimen by the steps imaging the three dimensional specimen; identifying target cells; registering the spatial parameters (x,y,z coordinates) of the target cells; and extraction of target cells according to their spatial parameters

4 Claims, 12 Drawing Sheets

METHOD FOR EXTRACTION OF TARGET CELLS FROM 3D TISSUE BY OPTICAL IDENTIFICATION

The present invention relates to a method for selecting cells or parts of cells or groups of cells with or without their extracellular matrix from a three dimensional specimen by optical identification of target cells and subsequent isolation of target cells.

Today one of the most promising approaches to cure cancer is immune cell therapy. The success of immune cell therapy is first and foremost visible in the field of circulating tumors like leukemia. The goal is to extend the current immune therapy approach to solid tumors.

The diversity of solid tumors is large in a single organism or organ and therapeutics has to face this diversity. Thus, it is important to be able to analyze tissue on cell-level individually. It is known that the interaction of the immune system with the tumor can be different at different sites within the organism. The understanding of this diversity and the adaptation of therapy even in a patient specific approach is important for the success of the therapy.

Biological tissue is a heterogenous assembly of cells. Some cells, parts of cells or groups of cells can most likely only be distinguished from other cells by their localization within a tissue (e.g. vessels lying next to a tumor, versus vessels next to unaffected tissue), combined properties within a group of cells exerted only as a group but not individually. For example, cancerous tissue such as ductal adenocarcinoma displays a disorganized tissue architecture while unaffected tissue shows an organized architecture (see FIG. 1) or glioblastoma show a very high density of cells expressing a combination of markers while unaffected neural tissue does not.

Cancer is a broad group of diseases involving unregulated cell growth. In cancer, cells divide and grow uncontrollably, forming malignant tumors, and invading nearby parts of the body. Cancer may also spread to more distant parts of the body through the lymphatic system or bloodstream.

Further, solid tumors or cancers tissues are usually surrounded or encapsulated by tumor microenvironment cells (TME), which consists of blood vessels, immune cells, fibroblasts, pericytes, signaling molecules and the extracellular matrix (ECM). ("NCI Dictionary of Cancer Terms". National Cancer Institute. 2011-02-02, for recent review see Am J Cancer Res. 2019; 9(2): 228-241).

The analyses of tissue in 2D using slices according standard procedures might not reveal the nature of the tissue and for instance a pathological assembly of cells. A three dimensional reconstruction of larger tissue areas, whole organs or organism with cellular resolution is at least very cumbersome and time consuming if not all impossible.

Further, tissue or organs can be dissociated so that the individual cells are available in suspension. Further analysis of the target cells can be performed by flow cytometry, flow sorting followed by single cell sequencing, microscopic approaches of even imaging flow cytometry. In this approach the morphological information is completely lost. Thus dissociation of tissues and subsequent analysis of single cells without prior spatial tagging can hardly be used to reconstruct three dimensional information.

Imaging of large tissue pieces using ultramicroscopy or other means has been described for example in "The light-sheet microscopy revolution", J M Girkin and M T Carvalho, Journal of Optics, Volume 20, Number 5 (https://iopscience.iop.org/article/10.1088/2040-8986/aab58a)

Extraction of cells from solid tissue has been described in the field. Cells can be extracted by submerging the tissue in a solution containing electrolytes, proteolytic enzymes, collagenases, proteases to digest the extracellular matrix. Other approaches use micro preparation like using micro-punches, microtome and micro scalpel or even laser micro dissection (https://eurekamag.com/research/066/022/066022108.php).

OBJECT OF THE INVENTION

Object of the invention was therefore to provide a method to select cells, parts, or group of cells by optical inspection, optionally tagging of selected areas and subsequent extraction of parts of interest.

Accordingly, first object of the invention is a process for extracting target cells from a three dimensional biological specimen by the steps
- a) imaging the three dimensional specimen
- b) identifying target cells
- c) registering the spatial parameters (x,y,z coordinates) of the target cells
- d) extraction of target cells according to their spatial parameters The method of the invention can be applied to any kind of tissue like an organism or a part of an organism such as an organ or a tumor. The subsequent analysis of the target cells may be performed by all state of the art.

The selection of cells i.e. identifying the target cells may be performed to create an artificially generated assembly of cells or may be directed to specific organs or tissue of cells like a solid tumor i.e. to a naturally occurring assembly.

Another object of the invention is an apparatus capable of performing the method, which is adjusted to extract target cells from a three dimensional biological specimen comprising an imaging unit for imaging the three dimensional specimen and identifying target cells; a data storage registering the spatial parameters (x,y,z coordinates) of the target cells and a means for extraction the thus identified target cells.

This patent application is directed to select single cell compartments or sub entities from a large entity of cells, e.g. tissue, tissue engineering products or cell cultures and to isolate these sub entities, i.e. to separate them from the tissue network, so that a further analysis of the target cells without loss of information on their location and/or intercellular environment (i.e. location within the surrounding tissue) becomes possible.

This publication also aims to show different processes in which the technology of separation from a large entity can be used for applications in medical research, diagnostics and therapy.

Definitions

In the following, the term "imaging the three-dimensional specimen" refers to any optical imaging method such as a light sheet microscope or any kind of confocal microscope, resulting in identifying target cells either by labelling (tagging) or by optical parameters like shape, appearance, fluorescence or refractive properties (so called intrinsic optical properties).

The term "IMAGING" modalities may include one or more of the following steps

Contrasts are taken with or without STAINING
i. Multi-Photon Microscopy (2-photon, 3-photon, SHG, THG, CARS)

ii. Confocal Microscopy including (laser scanning confocal microscopy, spinning disc microscopy, structured illumination microscopy, slit scanning microscopy, rescanning microscopy)

iii. Widefield microcopy including multi-staining approaches (e.g. MACSIma)

iv. Light sheet microscopy

The term "FURTHER ANALYSIS" may include one or more of the following steps i. Might include all IMAGING modalities ii. Flow Cytometry iii. Localization Super resolution microscopy (STORM, dSTORM, PAINT, DNA Paint, light sheet based localization microscopy, Localization microscopy using parallelized single molecule excitation (PSME))

iv. Other super resolution microcopy methods (STED, SIM, Super-resolution light sheet microcopy)

v. Cell separation techniques (magnetic cell separation, microvalve based separation, flow based separation) followed by analysis of the selected cells vi. Sequencing of RNA, CDNA, DNA including Single Cell Sequencing vii. Mass spectrometry viii. In-situ sequencing using one of the mentioned imaging techniques The term "target cells" is used synonymous with "parts of interest", "cell compartments", "sub entities", "sub volumes" or "compartments of interests" and may include one or more of the following i. Tissue (selected parts of the tissue: e.g.: Metastases, Tumor—Immune cell interaction areas of the tissue, subvolumes of the tissue)

ii. Colonies iii. Extracellular matrix iv. Cell-Cell interaction subareas (immunological synapse, cell membrane subareas)

v. Intracellular compartments (nuclei, ER)

The term "STAINING" or "TAGGING" may include one or more of the following methods i. Immunostaining with (Binders: Antibodies, FABs, Nanobodies, Aptamers, Peptides, recombinant MHCs, interacting protein domains conjugated with DNA/RNA coding sequences, DNA/RNA Origami multisite binding structures, gold particles, magnetic particles, chromophores, donor acceptor chromophore pairs, isotopes, tags (e.g. antigens such as Biotin), which can be bound by secondary binders)

ii. Photactivated crosslinked tags such a antigens which can be bound by binders or photoactivated crosslinked information carriers (barcodes) which can be read out to identify or isolate parts of interest. This can be for example nucleic acids (sequencing), spatial patterns (optics), etc.

iii. Intercalating stains iv. Genetically encoded dyes, light inducible crosslinkers, see above The term "PREPARATION" includes i. Mechanical and heat application Application of ultrasound, freezing, high pressure freezing, heating ii. Perfusion, diffusional treatment, electrophoretic infusion with one or several of the following substances Fixation agents (e.g. PFA, DMSO, THF, agents to stop RNA protease activities

STAINING

Substances which can be photoactivated (e.g photoswithcable dyes, dyes which can be bleached, photoactivable curing agents, multiphoton photoactivable curing agents. photoactivable crosslinkers Clearing agents Bleaching agents The term "ENCAPUSLATION" is directed to methods making the addressed volume resistant against optional tissue dissociation steps. The goal is to keep the morphology between the cells within the volume intact so that further detailed analysis of the target cells without loss of information on their location and/or intercellular environment (i.e. location within the surrounding tissue) becomes is possible.

After the group of cells of interest have been extracted from the specimen, the encapsulation agent can optionally be dissolved to isolate intact single cells. "ENCAPUSLATION" therefore may include one or more of the following steps:

i. Definition of the volume to be encapsulated ii. Optical cross-linking of the surface of the volume by means of photoactivable curing agents.

These agents may include all well-known strategies for light assisted hydrogel formation, UV-curable glues and 3D printing polymers.

iii. Optical cross-linking of the whole entire volume of the selected sub-compartment by means of photoactivable curing agents. These agents may include all well-known strategies for light assisted hydrogel formation, UV-curable glues and 3D printing polymers.

The term "Dissociation" may include mechanical or enzymatic dissociation of specimens, filtering of encapsulated material, magnetic separation manual dissection and separation.

"Localization microscopy" refers to the use of parallelized single molecule excitation (PSME)

BRIEF DESCRIPTION OF THE DRAWINGS

In the figures, the following reference signs are used:

100 Patient
101 Tumor
102 Micro biopsy
103 Dissociated tissue
104 Animal
105 Implanted tumor cells
106 Sample (whole mount animal or organ e.g. Animal brain with tumor(s)
107 Cell culture
108 Tissue culture
109 Encapsulated tissue
110 Tissue layers
111 Encapsulated sub-volume
112 Scanned tissue sub-volume
113 Tumor/immune-cell interaction site
114 Tumor cell
115 Antigen
116 Tagged antibody
117 Tagged antigen
118 Immune cell
119 Immunological synapse
200 Therapy or treatment
201 Adapted Therapy
300 Microscope e.g. light-sheet microscope
301 Light source
302 Light sheet
303 Objective
304 Sample holder
305 Slicing tool
306 Dissection tool 307 Micro dissection laser
308 Tagging light source (e.g. laser)
309 Encapsulation laser
310 Capsule
311 Tissue layers
312 Crosslinking
313 Particle
314 Treatment laser
315 Imaging
316 Detection
317 Treatment
318 Multiple ROI
319 Linescan
320 Multiple point
321 Light sheet formation optics
400 Further analysis
401 Imaging position
402 Preparation position
403 Advanced Imaging e.g. super resolution microscopy FIG. 1 shows the histology of a ductal adenocarcinoma of the pancreas.

FIGS. 10A-10B illustrate alternative configurations for tagging target cells before or after identification.

FIG. 16 provides a flowchart for the process steps in a labeled specimen embodiment.

SUMMARY OF THE INVENTION

In a first embodiment of the invention, the specimen to be imaged is not labelled prior imaging (step b) and only intrinsic optical properties are used to distinguish different parts and cells of the specimen. Spatial information, i.e. the locations as stored on the storage device, of the parts of interest in relation to the whole specimen, and knowledge of these locations is used to guide sectioning of the specimen for extraction of the parts of interest or for the preparation of slices for further analysis.

In a second embodiment, the specimen is labelled prior, during or after imaging (step b) to specifically label single cells, groups of cells or parts of a cell to register spatial information, i.e. storing the location, of such parts of interest and thus guide sectioning of the specimen for extraction of the parts of interest or for the preparation of slices for further analysis.

In a third embodiment, an optically inducible or cross-linking reagent is transferred to the specimen prior, during or after imaging and parts of interest are actively tagged by focusing light on the respective parts of interest.

The method of the invention can be applied to research applications, e.g. in immune cell therapy, where the dissolved components are then examined by further microscopic methods or, in the case of interest in genetics, in sequencing applications. The background is that very large tissue parts are available, e.g. in the context of surgical removal of tumor tissue, but that tumors of different genetic origin are present, which react differently to therapeutic approaches.

The invention is further directed to an apparatus which is configured to perform the different embodiments of the method of the invention. Exemplary workflows and protocols are provided in the section "Workflows and Protocols".

Figure 1:
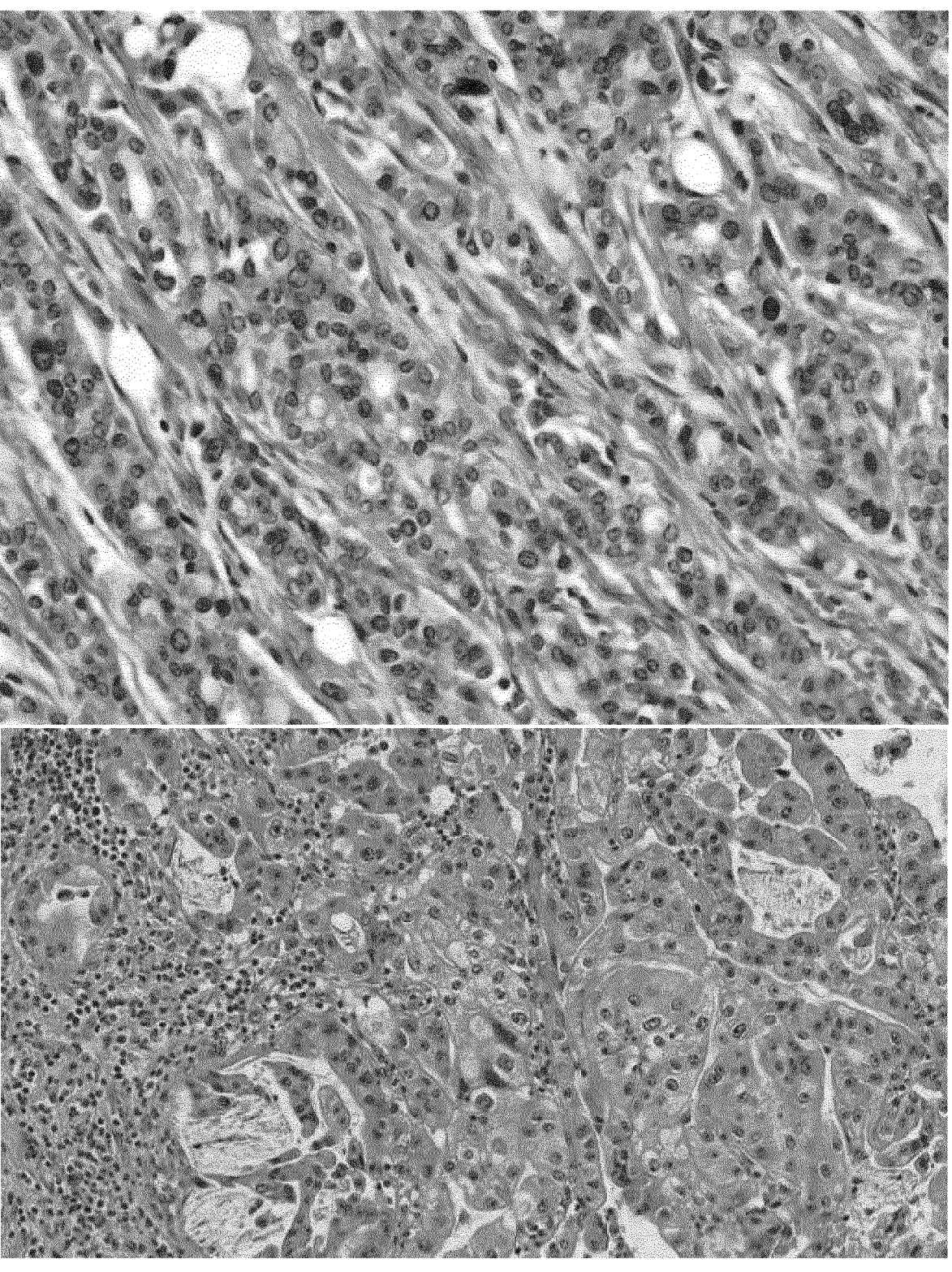
Figure 2:
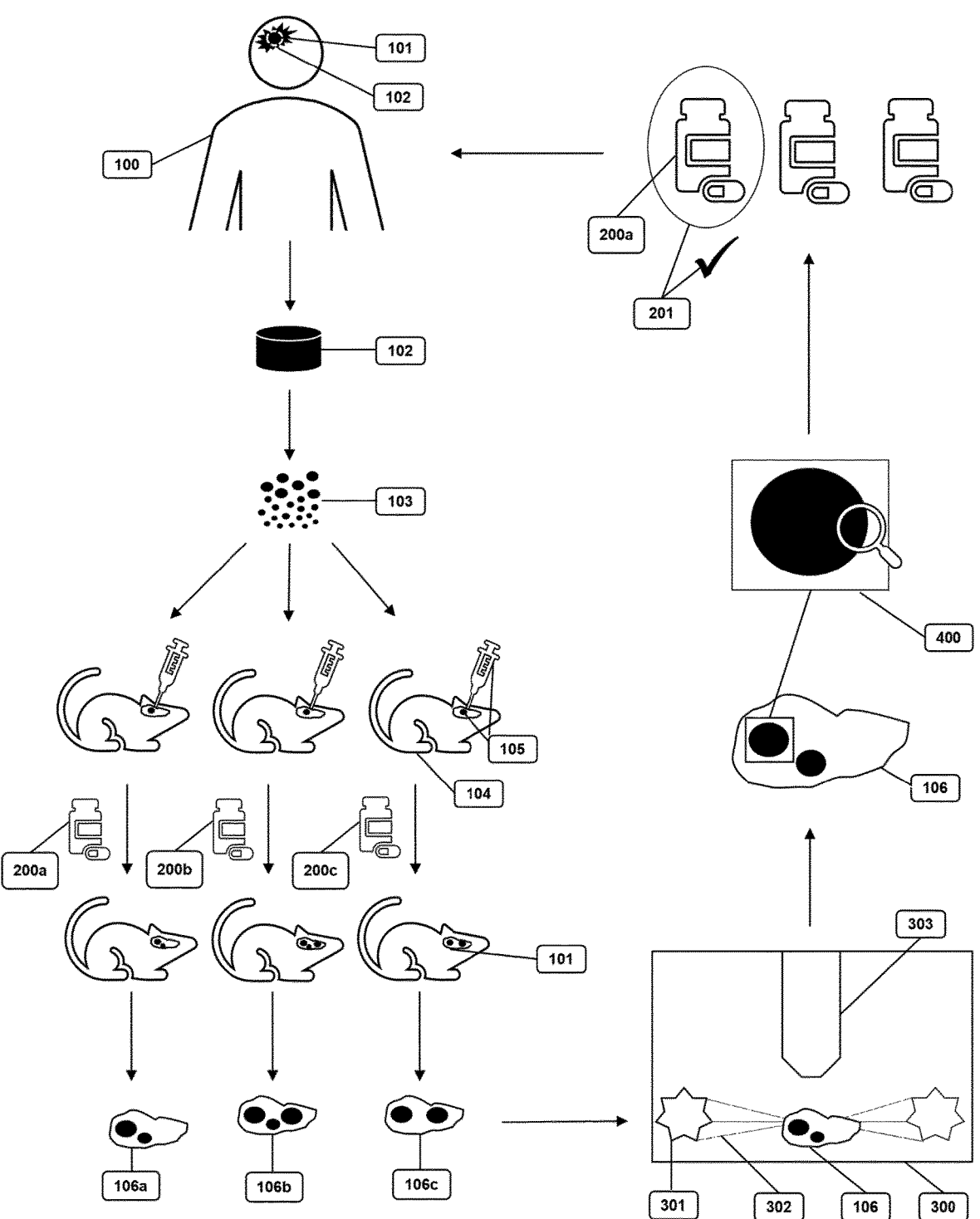
FIG. 2 shows a schematic overview of an embodiment of the process according to the invention, including imaging of the specimen. identification of target cells, registration of spatial parameters, and extraction.

As shown in FIG. 2, the method of the invention can be applied in a therapeutic workflow where a cancer patient (100) is undergoes surgical removal of a tumor (101). The explanted tissue (102) is than dissociated (103) and representative entities of cells are injected (105) into an (humanized) animal model (104). After a certain time of integration of the cells and tumor growth, the animals may undergo one or more different therapies (200 a-c). The most suitable therapy could then be applied to the patient. The organs (106 a-c) containing the tumor (101) are than explanted and prepared for microscopy. In this example light sheet microscopy (300) is used. Remaining tumor cells which are identified either due to labelling (staining) with tumor markers or by morphological recognition are extracted out of the organs (106 a-c) and further analysis can be applied to the micrometastasis. This may include further immunostaining, flow cytometry or microscopy, sequencing. This results into a second level individualized selected therapy (201) based on the assumption that the survival of the cells in the animal model under the first therapy is similar to the survival in the human.

Figure 3:
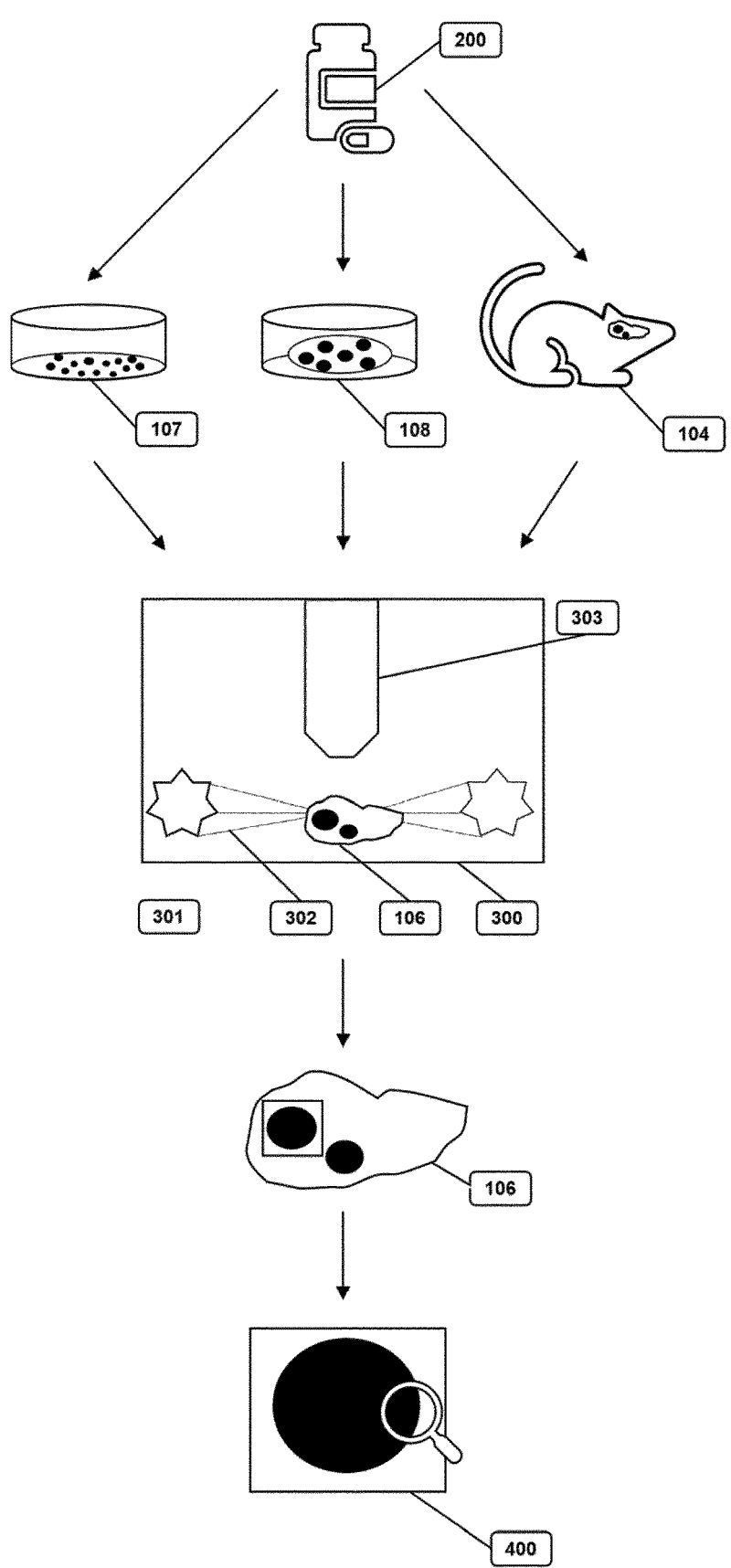
FIG. 3 illustrates an exemplary imaging unit configured as a light sheet microscope for three-dimensional imaging of the biological specimen.

FIG. 3 shows a workflow for research. A treatment (200) is applied to either a cell culture (107), tissue culture or tissue engineering product (108) or to an animal model (104). After incubation the sample is taken or the organ (106) is extracted and analyzed by microscope (303). Illumination is done in case of light sheet microscopy with light sheets (302) and light sources (301). The 3D-image is analyzed and after identification of the compartments of interests (cells, sub-cellular compartments or parts of the tissue) they are extracted and further analyzed (400).

Figure 4:
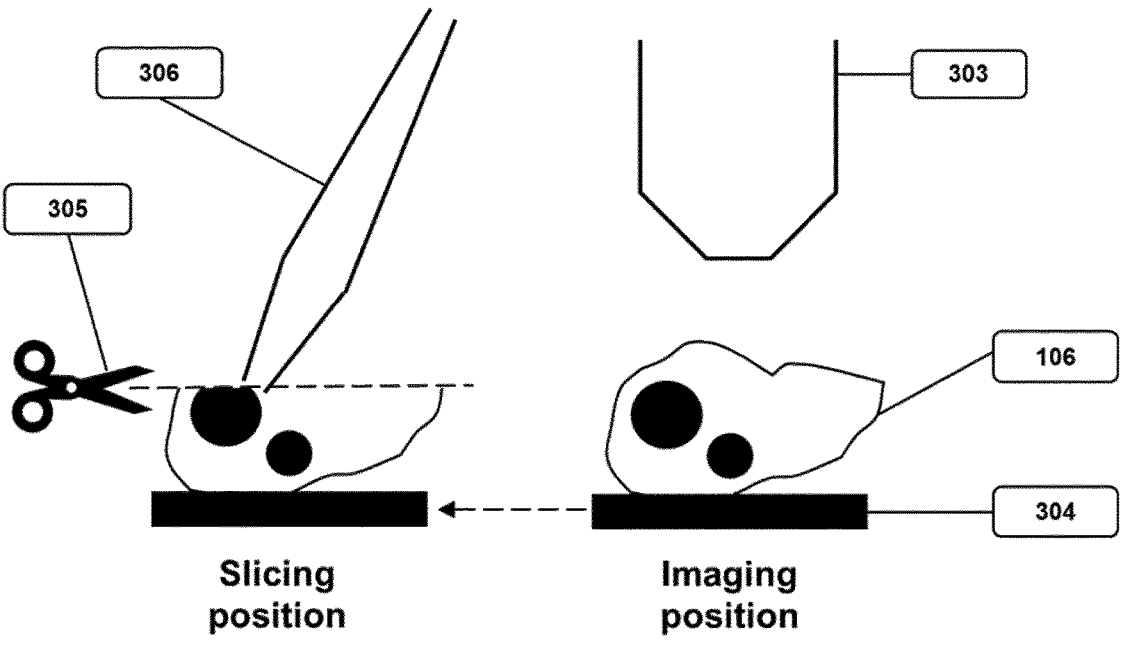
FIGS. 4-5 depict data processing steps for identifying target cells based on intrinsic optical properties or labeling.

FIG. 4 shows an embodiment where the extraction of the compartments of interest is done within a preparational light sheet microscope. In this embodiment, the tissue is moved between an imaging position under the objective (303) and a preparation position where the sample is sliced down to the level where one or more compartments of interested are located and can be reached for extraction. This embodiment comprises an appropriate sample holder (304) for holding the sample. A relative motion between the sample holder and the imaging and preparation position is possible. Subsequent imaging and slicing allows for a precise extraction of all selected sub-volumes.

Figure 5:
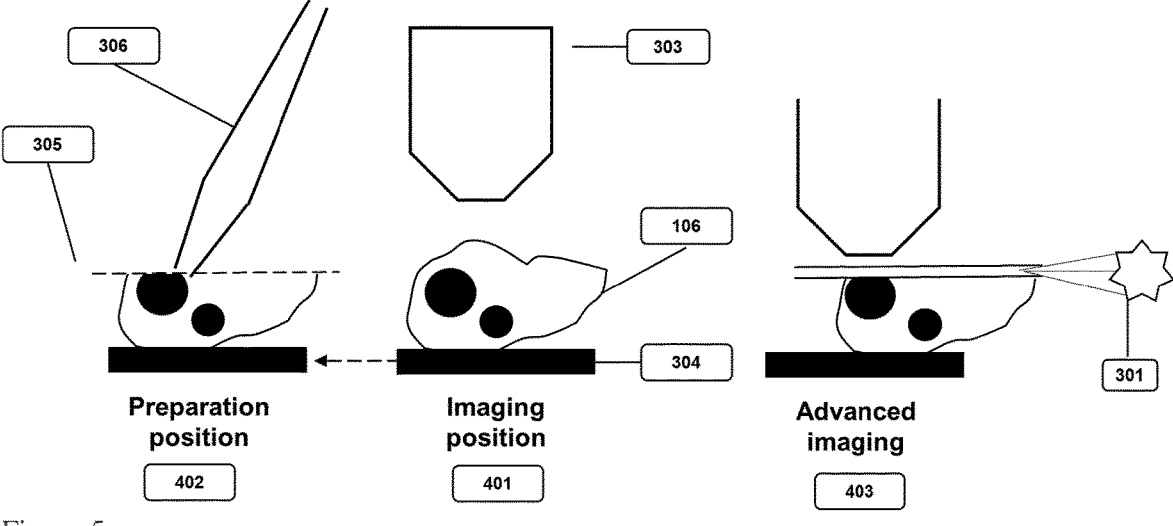

FIG. 5 shows an embodiment where the extraction of the compartments of interest is done within a preparational microscope (401), preferably a light sheet microscope (single plane illumination) due to its ability to provide high-resolution, non-destructive 3D imaging through selective plane illumination, which minimizes photodamage and enables precise identification and extraction of sub-volumes, or alternatively any kind of confocal microscope. The embodiment contains an imaging position under the objective (303) and a preparation position (402) to slice the sample down to the level where one or more compartments should be extracted. The embodiment includes a sample holder (304) for holding the sample. A relative motion between the sample holder (304) and the imaging and preparation position is possible. Subsequent imaging and slicing allows for a precise extraction of all selected sub-volumes. The embodiment further provides the possibility for a more detailed optical analysis (403). Within the process of subsequent imaging and slicing the sample is pressed to an waveguide or high refraction index glass which can be illuminated by means of a light source, preferentially a laser (301). Evanescent waves are used to obtain high or super-resolved images from the sample.

Figure 6:
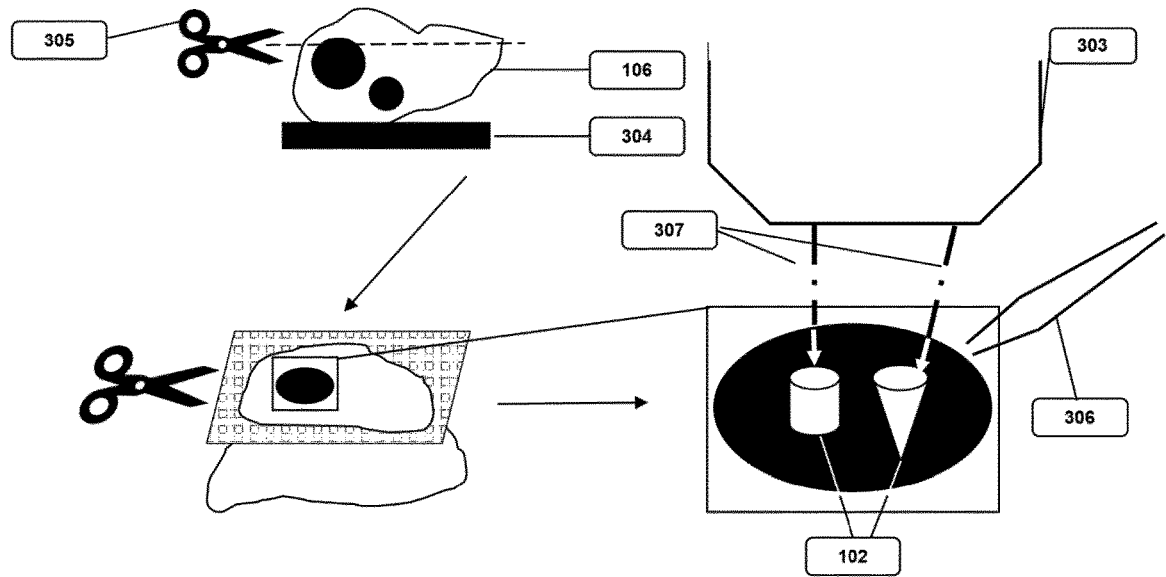
FIG. 6 shows the data storage component, implemented as a computer-readable memory or database, for registering the spatial parameters (x, y, z coordinates of identified target cells.

FIG. 6 shows another embodiment of the preparation and isolation of the compartments of interest. After slicing the sample (106) down to the region of interest (305) precise extraction of selected sub-volumes (102) is done by means of laser micro dissection (307). The cutting beam can be directed to the sample within arbitrary shape. In a variant, the dissection laser is coupled to the lens (303) at the margin of the aperture and scanned in a way to directly cutting a cone out of the sliced surface of the sample. In another variant, an arbitrary line is cut down to a certain depth (10 to 200 µm). Further slicing (305) or direct extraction (306) releases and collects the sub volume or cell.

Figure 7:
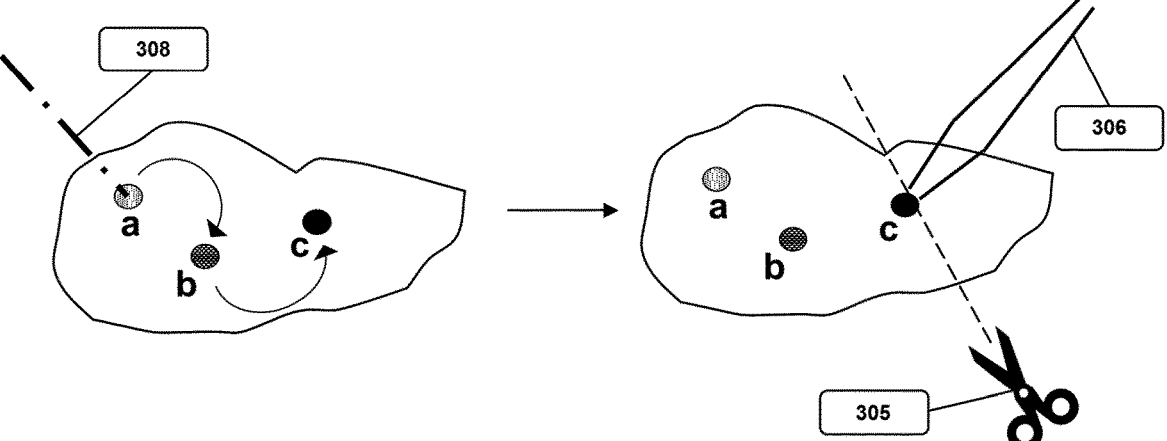
FIG. 7 illustrates the means for extraction, comprising a laser configured to ablate or capture the identified target cells according to their registered spatial parameters, in combination with an image sensor for guiding the extraction.

FIG. 7 shows another embodiment where a tagging light source (308) is directed to the selected sub compartments of interest. Optical tagging opens the possibility to tag different sub compartments (a,b,c) (e.g. metastasis of cells) individually. Identification or enumeration of target cells can be achieved by different intensities or colors or shape of the tagged objects. In the case of two or more different photo-activable dyes, an activation level could be predefined as threshold set and the tagging could be done by generating different ratios between the dyes. An in-situ check of the tagging intensities and ratios is possible since the marking is done within the imaging instrument directly. The tagging could be done either by nonlinear activation of the switchable molecules by means of multi-photon activation or by one photon laser scanning activation. The focusing of the light can be done by special light modulators sequentially or simultaneously or in a similar way by direct projection with a DLP-device. The further processing of the sample could be done by dissection (305) under optical control and extraction of the tagged sub compartments (306)

Figure 8:
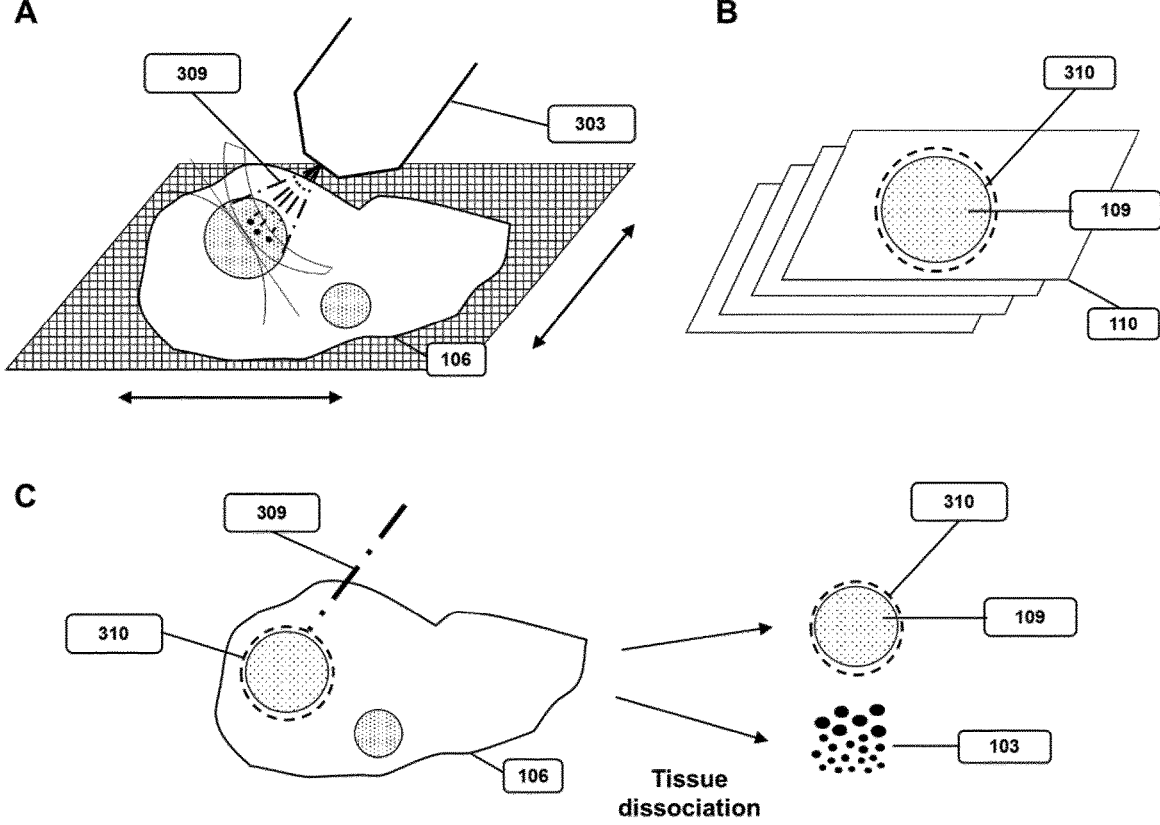
FIG. 8 depicts an embodiment wherein the three-dimensional specimen is provided with an optically inducible crosslinking reagent prior to or during imaging.

In another embodiment shown in FIG. 8, the sample (106) is prepared in a way that optical crosslinking (309) of tissue fragments is used to maintain the morphological structure of the target cells. This embodiment includes the extraction of the encapsulated compartments (310) to make them assessable to further microscopic approaches optionally involving rehydration and multiple label imaging.

The encapsulation or crosslinking process could be done either by nonlinear activation of the crosslinking by means of multi-photon activation or by one photon laser scanning activation. The focusing of the light can be done by special light modulators sequentially or simultaneously or in a similar way by direct projection with a DLP-device. The crosslinking process can be performed directly within a light sheet microscope where the detection lens can be used to direct the crosslinking laser (309) to the sample. Encapsulation or crosslinking methods are known to the person skilled in the art and are for example disclosed in "Advances in crosslinking strategies of biomedical hydrogels", Wu et al., Biomater Scie, 2019 (The Royal Society of chemistry)

Figure 9:
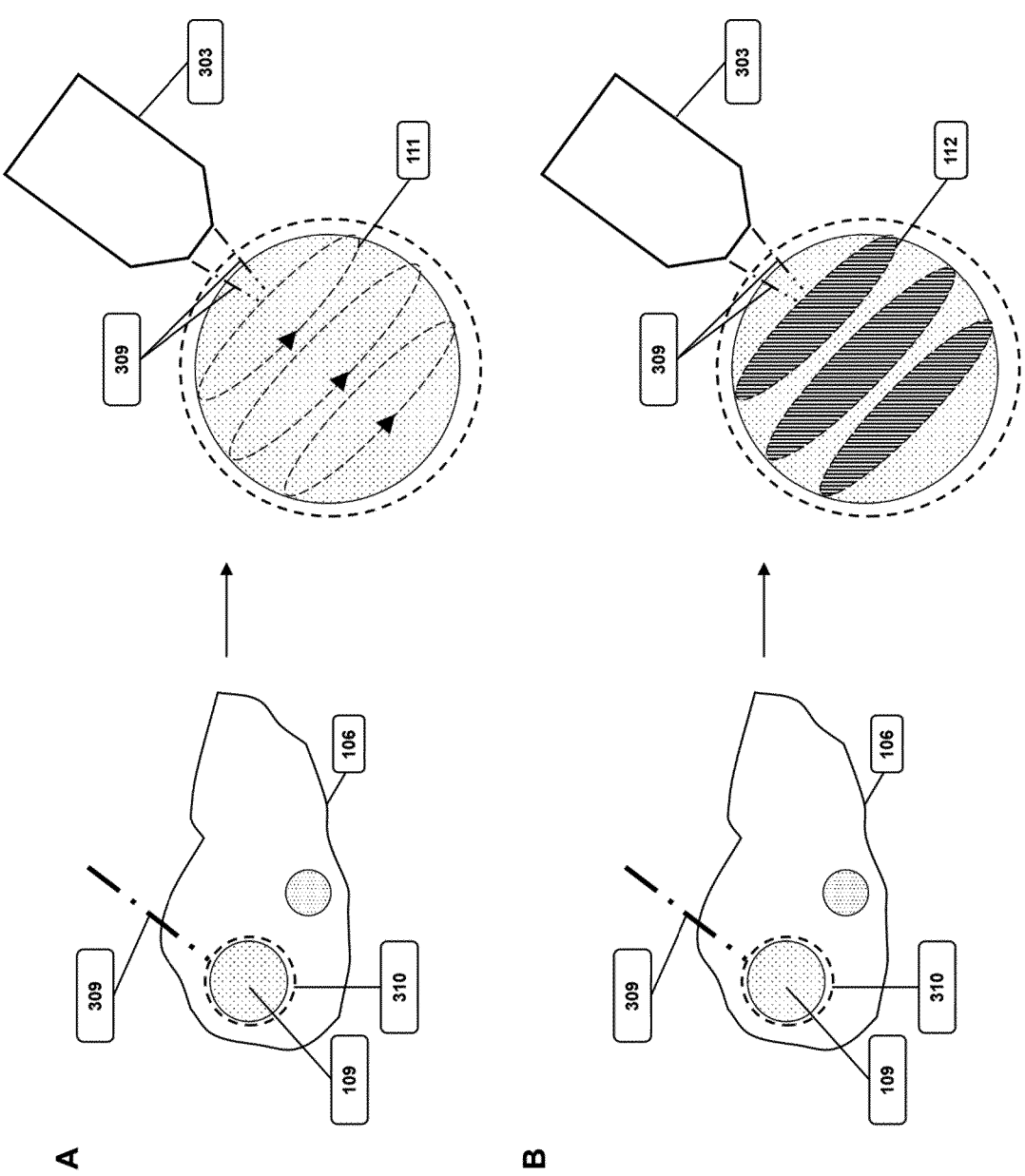
FIGS. 9A-9C show sectional views of the specimen during extraction, highlighting the movement of the laser to the target cell location based on spatial coordinates.

FIG. 9 shows two different embodiments of the invention where a light sheet microscope 303 (for example a tilted light sheet microscope) is used to analyze and subsequently mark or treat target cells in combination with laser scanning. The laser is directed through the detection objective. Since the treatment of the plane is also assessable by the light sheet at the same time, optical control of the process is possible. (A) shows an encapsulation process where a margin of the sub volume is addressed layer by layer with the encapsulation laser (309). (B) shows a protocol where different layers addressed after imaging as a whole volume layer by layer. This in to crosslinking of a sub-volume could be used to immobilize the morphological structure.

Figures 10, 11:
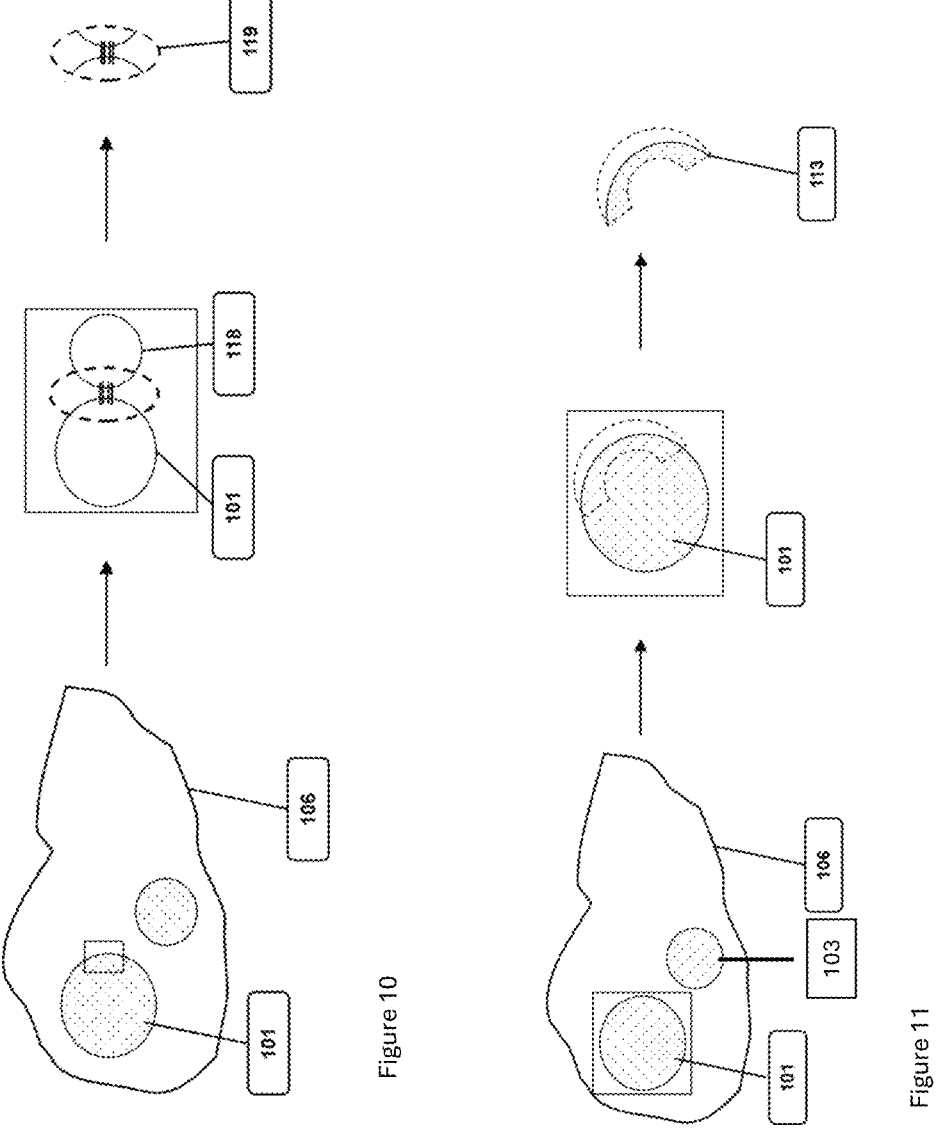
FIG. 11 represents the overall apparatus integration, including the imaging unit, data storage, and extraction means.

FIG. 10 shows the extraction of interaction zones between tumor (101) and immune cells (103) such as tumor microenvironment cells (TME). Further analysis can be used to understand the mechanisms of the attack and defense of e.g. CAR-T cells. And might be used to optimize CAR-T cell therapy especially by weakening the defence mechanisms by supplementary medication. This could be also used to support personalized therapy.

FIG. 11 shows an example where crosslinking could be used in the analysis of cell compartments comprising an ensemble of immunological synapses. The crosslinking of the two cells (e.g. tumor cell (101) and immune cell (118) allows an extraction of a fixed but morphologically intact immunological synapse. It could be also possible to isolate the volume containing the synapse. Further analysis could than include super-resolution microscopy to quantify the molecule exposed within the immunological synapse.

Figure 12:
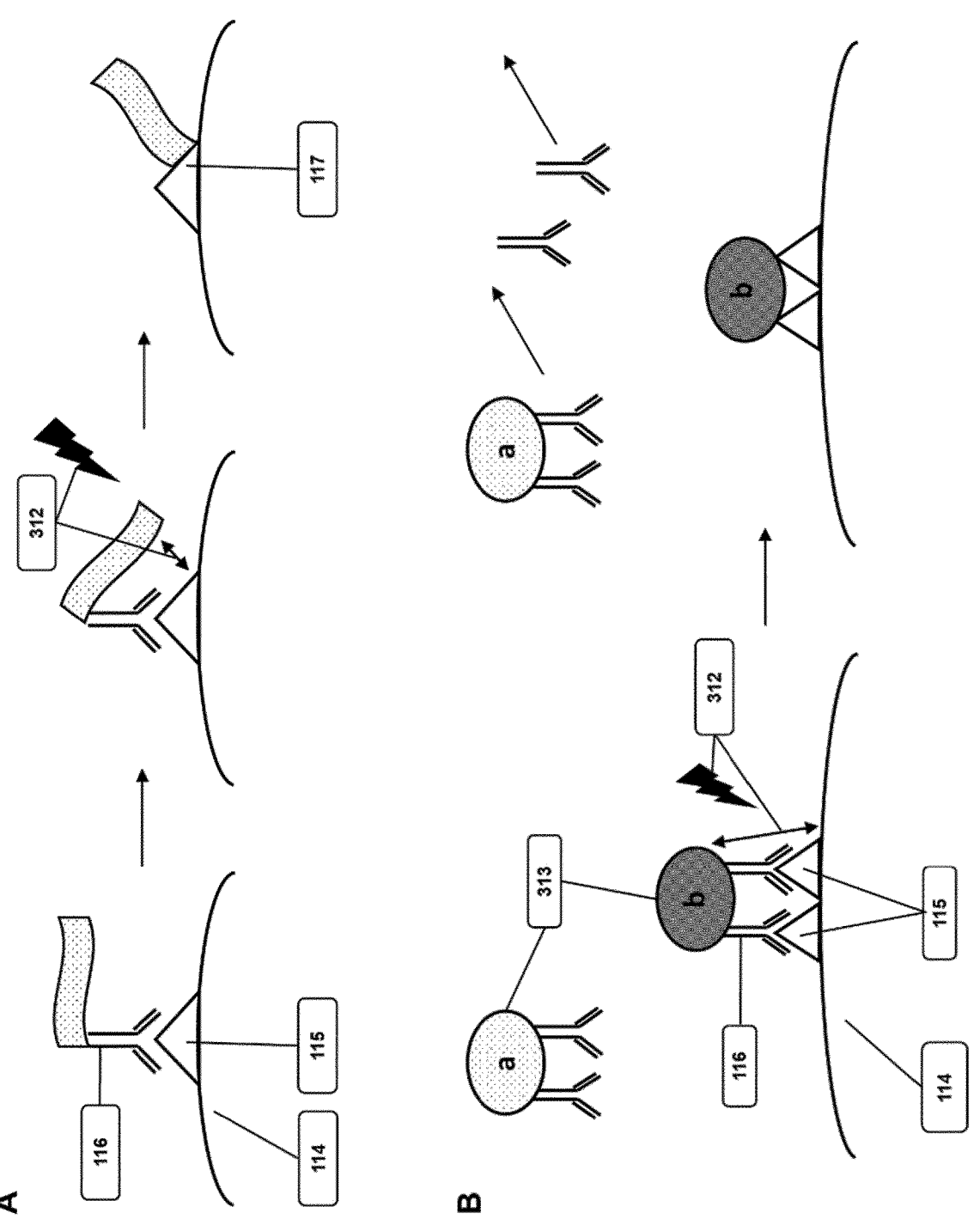
FIG. 12 shows a workflow for using intrinsic optical properties for cell identification.

FIG. 12A shows the variant of the invention where crosslinking of DNA/RNA strands conjugated to an antibody to the cell offers the possibility to mark cells with a code or make the cell visible for DNA-PAINT Microscopy. FIG. 12 B shows the crosslinking of magnetic beads to a cell surface or compartment followed by a washing step to remove all beads which are not cross-linked. The dissociated sample can than separated by magnetic cell separation.

Figure 13:
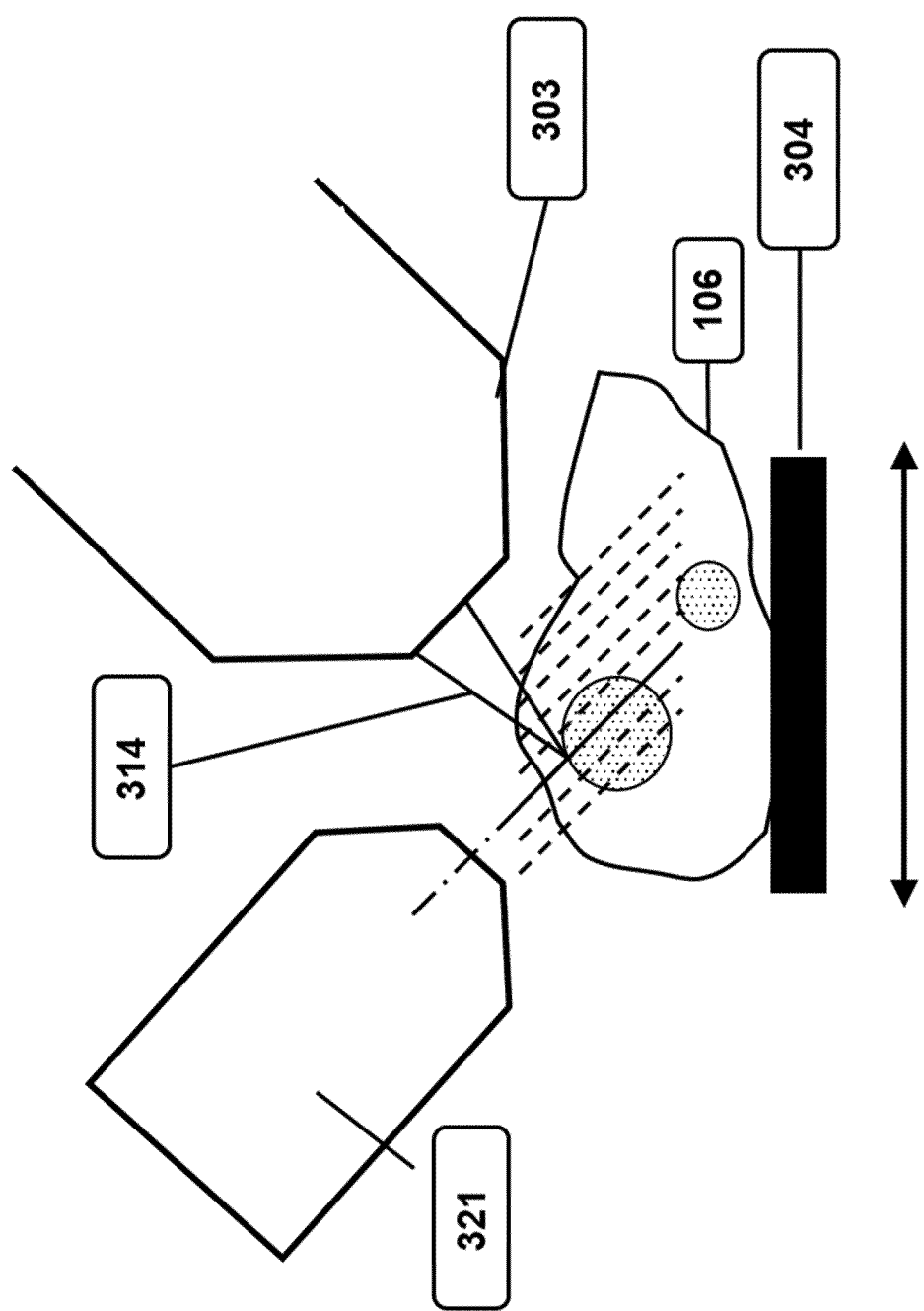
FIGS. 13A-13B depict examples of spatial parameter registration in a coordinate system.

Another embodiment is depicted in FIG. 13, where the sample (106) is mounted on a sample holder (304). The sample holder is movable relative to the optics. The embodiment forms a tilted light-sheet (321). The image is detected through the objective (303) perpendicular to the light sheet. The system is combined with a photo treatment laser (314) which is applied through the imaging optic. In this configuration, subsequent imaging, treatment and stepping of the relative position between the sample holder and the optics allows to address large volumes as long as the sample is sufficiently thin.

Figure 14:
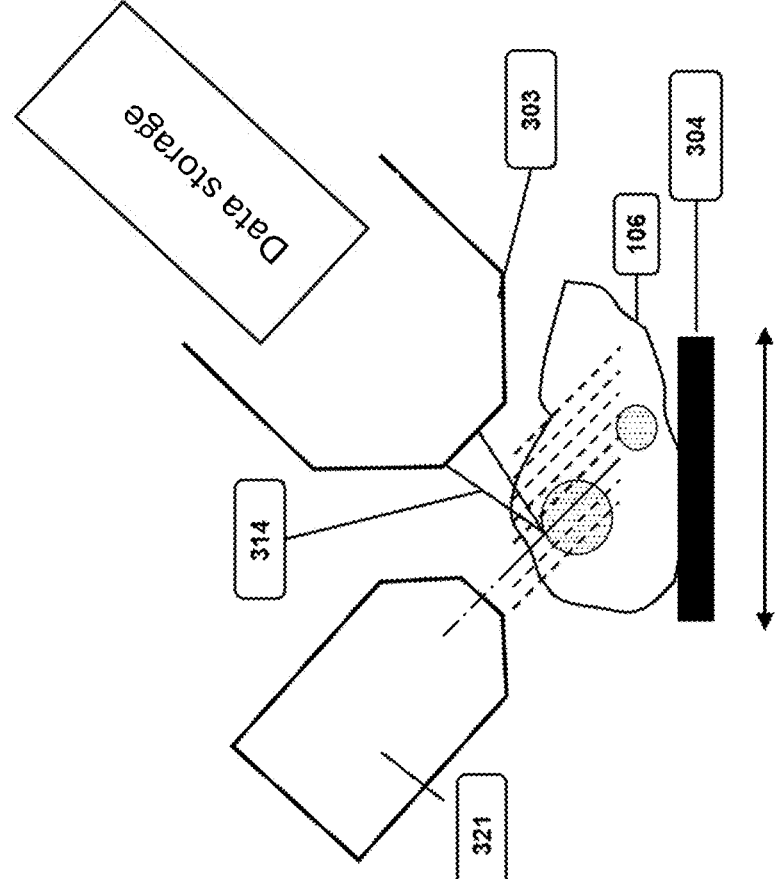
FIG. 14 illustrates post-extraction analysis of isolated cells.

FIG. 14 shows by way of example the embodiment of the invention where a sliced surface of a cleared sample is imaged with multi photon microscopy. Part A of FIG. 14 shows in the middle a cell being located about 5 µm under the cutting plane. In FIG. 14, a top view of the slightly tilted cutting plane is depicted. Clearing was performed using Dibenzyl-ether. The cutting was performed with a conventional microtome.

Figure 15:
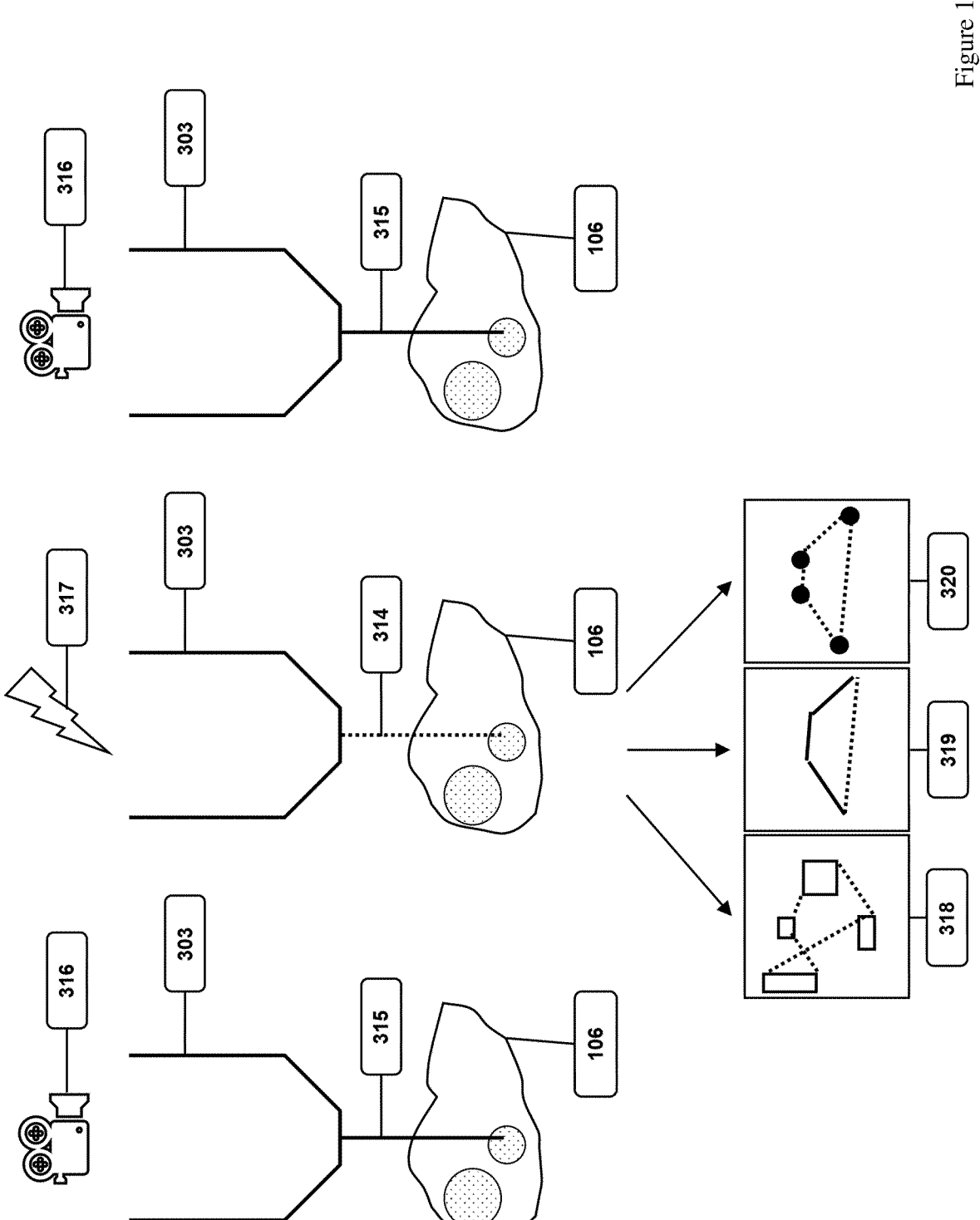
FIGS. 15A-15B show variations in the extraction means using one-photon or multi-photon laser activation.

FIG. 15 shows an laser scanning treatment protocol where a series (316) of acquisitions (315) is interrupted and either multiple regions of interest (318), combinations of lines (319) or a series of points (320) are treated (317). The treatment allows for not only structured photoactivation or crosslinking but also a marking, where the individual structures can be identified through the geometry of treatment. In case the subsequent analysis of the sub-compartments is again a microscopic method. Data generated in this analysis step could be correlated to the initial imaging process, so that the detailed analysis could be viewed in the context of the whole sample which can be also the complete organism.

In all disclosed embodiments of the method of the invention, subsequent extraction of compartments can be done. Super-resolution can be obtained with PAINT, dSTORM and DNA-PAINT. Staining procedures can be applied sequentially after sectioning or up front during the preparation the sample. By this means it is possible to combine the slicing with further analysis and super-resolution microscopy approaches, where the penetration of the light and also diffusion of reagents is or should be limited to the surface of the sample.

Further, all disclosed embodiments of the method of the invention may involve chemical dissociation of the tissue and subsequent collection of the optically tagged sub-compartments. A back tracing of individual tagged compartments to its location within the sample is possible even in a situation where the sample is completely destroyed (disassembled) and dissolved for example with a gentleMACS instrument. The disassembly process can be speeded up by dissecting the tissue to a reasonably large number of slices. It is possible to design the slicing in a way that the tagged compartments are not destroyed.

In addition, all disclosed embodiments of the method of the invention may involve further analyzing the encapsulated entity by means of sequencing. It is also possible to further dissociate the encapsulated compartment and to analyze the individual cells contained in the compartment. Thus differentiation between different interaction zones between tumor in its microenvironment is possible. The extraction of the encapsulated volumes can be done by means of slicing and preparation, where the preparation is supported by the crosslinking of the capsule. The extraction of the capsules could be also done by tissue dissociation where the crosslinking is designed in a way that is withstands the dissociation process.

Workflows and Protocols

Workflows
  i. Therapeutic workflow
    Surgery—(Dissociation)—Implantation—Therapy I—IMAGING I—TARGET SELECTION—FURTHER ANALYSIS—adapted Therapy II
  ii. Research workflow
    Tissue culture, co-culture, model animals under different preparational or treatment conditions—Whole animal imaging—Tissue extraction and PREPARATION—IMAGING I—TARGET SELECTION—FURTHER ANALYSIS
  iii. Diagnostic workflows
    Biopsy taken from a patient in preparation for a treatment of during treatment. Fully automated IMAGING I and TARGET SELECTION process as outlined in the research workflow. FURTHER ANALYSIS is than used to characterize and quantify the targets.

Selection Protocols
  i. Imaging—TARGET identification—slicing—extraction of targets
  ii. Imaging—TARGET identification—slicing—LASER-CUTTING—slicing—extraction of targets
  iii. Imaging—TARGET identification—laser MARKING—slicing—picking
  iv. Imaging—TARGET identification—laser ENCAPSULATION—dissociation—extraction of targets
  v. Imaging—target identification—SUB-VOLUME laser preparation—dissociation
  vi. Imaging—target identification—digestion and/or mechanical disruption—isolation of undigested (encapsulated) parts of interest by size (filter), density (centrifugation), stiffness SUB-VOLUME laser preparation—dissociation

The invention claimed is:

1. A process for extracting target cells directly from a three dimensional biological specimen by comprising the steps;
  a) imaging the three dimensional specimen using a light sheet microscope, the light sheet microscope including a detection lens;
  b) identifying target cells and determining spatial information (x,y,z coordinates of the target cells;
  c) storing the spatial information of the target cells; and
d) extracting the target cells according to their stored spatial information,
  wherein the three dimensional specimen is provided with an optically inducible crosslinking reagent in at least one of the steps a), b), c) or d) and the optically inducible crosslinking reagent is crosslinked by activation by a one-photon crosslinking laser,
  wherein the detection lens of the light sheet microscope is used to direct the crosslinking laser onto the three dimensional specimen.

2. Process according to claim 1, wherein the target cells are tagged before or after step b).

3. Process according to claim 1 wherein the target cells are identified in step b by their intrinsic optical properties.

4. Apparatus for extracting target cells directly from a three dimensional biological specimen comprising:
  an imaging unit including that includes a light sheet microscope configured to image,
  identify and determine spatial information (x,y,z coordinates) of the target cells in the three dimensional specimen, wherein the light sheet microscope includes a detection lens;
  a one-photon crosslinking laser configured to provide light activation;
  a data storage device configured to store the spatial information of the target cells; and
  a means for extraction of the identified target cells;
  wherein the three dimensional specimen includes an optically inducible crosslinking reagent and the optically inducible crosslinking reagent is crosslinked by activation using the one-photon crosslinking laser,
  wherein the one-photon crosslinking laser uses the detection lens of the light sheet microscope to direct activating light onto the three dimensional specimen.

* * * * *